US012668779B2

(12) United States Patent
Zhou et al.

(10) Patent No.: US 12,668,779 B2
(45) Date of Patent: Jun. 30, 2026

(54) METHOD FOR IN VITRO EXPANSION OF CRYOPRESERVED CORD BLOOD-DERIVED REGULATORY T CELLS (Tregs) WITH HIGH RECOVERY RATE

(71) Applicant: CENTRAL SOUTH UNIVERSITY, Changsha (CN)

(72) Inventors: Zhiguang Zhou, Changsha (CN); Haibo Yu, Changsha (CN)

(73) Assignee: CENTRAL SOUTH UNIVERSITY, Changsha (CN)

( * ) Notice: Subject to any disclaimer, the term of this patent is extended or adjusted under 35 U.S.C. 154(b) by 0 days.

(21) Appl. No.: 18/992,204

(22) PCT Filed: Jul. 6, 2023

(86) PCT No.: PCT/CN2023/106036
§ 371 (c)(1),
(2) Date: Jan. 8, 2025

(87) PCT Pub. No.: WO2024/008140
PCT Pub. Date: Jan. 11, 2024

(65) Prior Publication Data
US 2025/0263660 A1 Aug. 21, 2025

(30) Foreign Application Priority Data
Jul. 8, 2022 (CN) ........................ 202210805505.X

(51) Int. Cl.
*C12N 5/0783* (2010.01)
*C12N 5/00* (2006.01)

(52) U.S. Cl.
CPC ........... *C12N 5/0637* (2013.01); *C12N 5/525* (2025.01); *C12N 5/562* (2025.01); *C12N 2500/90* (2013.01)

(58) Field of Classification Search
None
See application file for complete search history.

(56) References Cited

FOREIGN PATENT DOCUMENTS

| | | |
|---|---|---|
| CN | 104278012 A | 1/2015 |
| CN | 104357389 A | 2/2015 |
| CN | 107349219 A | 11/2017 |
| CN | 115305236 A | 11/2022 |
| WO | 2009021995 A1 | 2/2009 |
| WO | 2011126806 A1 | 10/2011 |

OTHER PUBLICATIONS

Gołąb et al., Oncotarget, 2018, vol. 9, (No. 11), pp. 9728-9740 (Year: 2018).*
Kokaji et al Releasable Rapidspheres: Human regulatory T cell isolation in 55 minutes using EasySep™ Releasable RapidSpheres™ (TECH2P.912), The Journal of Immunology, vol. 194, Issue 1_Supplement, May 2015, p. 206.22 (Year: 2015).*
Stemcell Technologies EasySep Release Protocol Feb. 4, 2018 (8 pages), retrieved from the internet: https://web.archive.org/web/20180204065040/https://www.stemcell.com/easysep-release (Year: 2018).*
Stemcell EasySep Human CD4+CD127lowCD25+ Regulatory T Cell Isolation Kit (5 pages), retrieved from the internet:https://cdn.stemcell.com/media/files/pis/10000023454-PIS_02.pdf (Year: 2025).*
English Translation of CN 107349219, 6 pages (Year: 2017).*
Clarke et al (Stemcell Technologies) (Oct. 24, 2025); retrieved from the internet: https://cdn.stemcell.com/media/files/poster/SP00158-Releasable_RapidSpheres_Enable_Immunomagnetic_Purification_of_Highly_Viable_and_Functional_Immune_Cells_from_Complex_Tissues_in_Less_Than_30_Minutes.pdf (Year: 2025).*
Kaiser et al., Frontiers in Cell and Developmental Biology, Dec. 2021, vol. 9, Article 750286, 12 pages (Year: 2021).*
CellTrace™ CFSE Cell Proliferation Kit, for flow cytometry, Thermo Fisher Scientific, retrieved from: https://www.thermofisher.com/order/catalog/product/C34554.

* cited by examiner

*Primary Examiner* — Evelyn Y Pyla
(74) *Attorney, Agent, or Firm* — Bayramoglu Law Offices LLC

(57) ABSTRACT
A method for in vitro expansion of cryopreserved cord blood-derived regulatory T cells (Tregs) with a high recovery rate is provided, including the following steps: recovering the cryopreserved cord blood-derived Tregs after first expansion, and resuspending the cells with a serum-free medium; and adding a resulting suspension to an expansion culture medium, and conducting a second expansion culture, where a primary culture is conducted for 1 d to 2 d, then a subculture is conducted once every 1 d to 3 d, and a total culture time is 13 d or more. In the expansion culture medium, interleukin-2 (IL-2) is further added. The method can achieve the second recovery and expansion of cryopreserved Tregs produced after the first expansion. Tregs produced after the second recovery and expansion can have a viability of 90% or more, and can be further expanded (such as third expansion and fourth expansion).

2 Claims, 5 Drawing Sheets

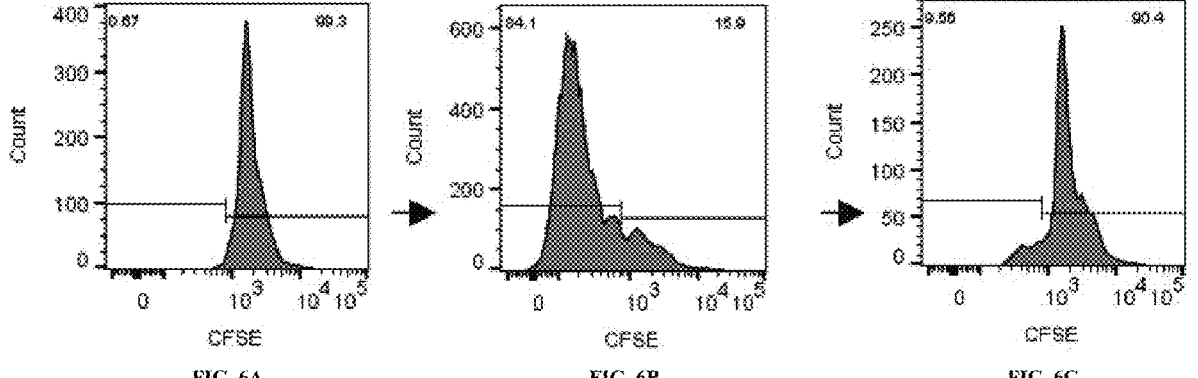
FIG. 6A                    FIG. 6B                    FIG. 6C

METHOD FOR IN VITRO EXPANSION OF CRYOPRESERVED CORD BLOOD-DERIVED REGULATORY T CELLS (Tregs) WITH HIGH RECOVERY RATE

CROSS REFERENCE TO THE RELATED APPLICATIONS

This application is the national phase entry of International Application No. PCT/CN2023/106036, filed on Jul. 6, 2023, which is based upon and claims priority to Chinese Patent Application No. 202210805505.X, filed on Jul. 8, 2022, the entire contents of which are incorporated herein by reference.

TECHNICAL FIELD

The present disclosure belongs to the field of cell therapy, and in particular relates to a method for in vitro expansion of cryopreserved cord blood-derived regulatory T cells (Tregs) with a high recovery rate.

BACKGROUND

Immune diseases involve the impaired functions of various organs and tissues caused by autoimmune disorders in patients, and have a wide disease spectrum, including autoimmune diabetes, systemic lupus erythematosus, etc. Autoimmune diseases are also listed as one of the ten major diseases in the Outline of the National Program for Medium- and Long-term Science and Technology Development of China. China has a large population base and a large absolute number of patients. Immune diseases not only impose a heavy economic burden on individuals and families, but also cause a serious impact on the economic development in China. The current treatments for immune diseases mostly rely on the traditional methods such as immunosuppressants. However, the immunomodulatory disorders as a main cause for immune diseases have not been solved.

Regulatory T cells (Tregs) are a special T cell subset that maintains the dynamic immune homeostasis by inhibiting and regulating effector T cells. Since the isolation and identification of Tregs by Japanese scholars at the end of the last century, Tregs have become a hot topic in the research of immunity in recent years. A variety of clinical trials related to Tregs have been initiated outside China. The representative Treg therapy for graft versus host disease has confirmed the safety and efficacy of Treg therapy in treating immune diseases. However, Treg therapy for immune diseases is still blank in China. Treg therapy can restore the balance of the immune system to prevent the further damage of autoimmune responses to organs and tissues and improve or even reverse a disease state, thereby fundamentally curing an immune disease.

More and more studies have shown that the cord blood is rich in Tregs, which are mostly Naïve T cells because these Tregs are not activated by antigens. Tregs expanded in vitro have excellent functions and low immunogenicity, which brings new hope for the treatment of immune diseases. At an early stage, the team of the present disclosure has established an in vitro isolation, expansion, and functional identification method for cord blood-derived Tregs that was approved as a national invention patent (patent No.: 201710613737.4), has carried out the clinical study of treating autoimmune diabetes with cord blood-derived Tregs for the first time internationally, and has preliminarily clarified the safety and efficacy of cord blood-derived Tregs in the treatment of autoimmune diabetes. In 2019 and 2020, the Juvenile Diabetes Cure Alliance (JDCA) published the annual reports on the global technologies for treating type 1 diabetes, respectively. The "cord blood-derived Treg" therapy technology has continuously been rated as the leading technology worldwide. Globally, there is currently no clinical trial for using cord blood-derived Tregs to treat an immune disease. Tregs can be extracted from the cord blood, expanded, and then used, which takes 14 d to 21 d. Thus, the clinical on-demand access requirement cannot be met. When the cryopreserved Tregs are recovered and then expanded, the cells will die in large quantities, which seriously affects the clinical use of Tregs. Therefore, it is urgent to establish an optimized method for in vitro expansion of cryopreserved Tregs with a high recovery rate and establish a Treg bank, thereby meeting the needs of clinical patients.

SUMMARY

A technical problem to be solved by the present disclosure: A method for in vitro expansion of cryopreserved cord blood-derived Tregs with a high recovery rate is provided to overcome the deficiencies and shortcomings mentioned in the above background.

In order to solve the above technical problem, the present disclosure provides the following technical solutions:

A method for in vitro expansion of cryopreserved cord blood-derived Tregs with a high recovery rate is provided, including the following steps:

(1) recovering the cryopreserved cord blood-derived Tregs after first expansion, and resuspending the cells with a serum-free medium to produce a suspension; and (2) adding the suspension to an expansion culture medium, and conducting a second expansion culture, where a primary culture is conducted for 1 d to 2 d, then a subculture is conducted once every 1 d to 3 d, and a total culture time is 13 d or more, where in volume fractions, the expansion culture medium includes 70.54% to 85.27% of a serum-free medium, 2.5% to 5% of a 4-hydroxyethylpiperazine ethanesulfonic acid buffer, 1% to 2% of a penicillin-streptomycin solution, 1% to 2% of L-glutamine, 50 μmol/L to 100 μmol/L of 2-mercaptoethanol, 0 U/mL to 1,000 U/mL of recombinant interleukin-2 (IL-2), 50 nmol/L to 200 nmol/L of rapamycin, and 10% to 20% of AB serum.

In the method for in vitro expansion of cryopreserved cord blood-derived Tregs with a high recovery rate, preferably, a process of producing the cryopreserved cord blood-derived Tregs after the first expansion includes the following steps: preparing Tregs, adding an expansion culture medium to Tregs carrying magnetic beads, and conducting a first expansion culture, where a primary culture is conducted for 1 d to 2 d, then a subculture is conducted once every 1 d to 3 d, and a total culture time is 18 d or more.

Preferably, a process for the preparing Tregs includes the following steps:

S1, isolating a peripheral blood mononuclear cell (PBMC) layer from cord blood, removing red blood cells with a red blood cell lysis buffer, washing, and counting; conducting centrifugation, removing a resulting supernatant, and cryopreserving; and recovering and counting; and S2, conducting centrifugation, removing a resulting supernatant, and resuspending cells with an Easy Buffer to produce 0.5 mL to 6 mL of a suspension with a cell concentration of $5\times10^7$ cells/mL; and S3, transferring the cord blood-derived Treg-containing suspension into a sterile tube matching with a magnetic pole, adding CD25 Positive Selection Cocktail, and incubating for 5 min; vortexing Releasable RAPID-SPHERE™ for 30 s or more until magnetic bead aggregates disappear; adding the Releasable RAPID-SPHERE™, adding a $CD4^+$ T cell enrichment antibody mixture, and incubating for 5 min; adding an Easy Buffer to 10 mL, and gently mixing 2 times to 3 times; placing the sterile tube on the magnetic pole, and incubating for 10 min; preparing a centrifuge tube to collect $CD25^-$ cells, and pouring a liquid in the sterile tube into the centrifuge tube under the magnetic pole; removing the sterile tube from the magnetic pole, adding 10 mL of an Easy Buffer to the sterile tube, gently mixing 2 times to 3 times, placing the sterile tube on the magnetic pole, and incubating for 5 min; adding an Easy Buffer to the initial resuspension volume with all cells on a tube wall rinsed off; adding a magnetic bead-removing buffer; adding a $CD127^{high}$-removing antibody mixture, and incubating for 5 min; adding an Easy Buffer to 10 mL, and thoroughly mixing 2 times to 3 times; placing the sterile tube on the magnetic pole, and incubating for 5 min; and preparing a centrifuge tube to collect Tregs, and pouring a liquid in the sterile tube into the prepared centrifuge tube under the magnetic pole. The Releasable RAPID-SPHERE™ can be releasable magnetic bead or releasable magnetic particles and the Easy Buffer, e.g., Easy-Sep™ can be magnetic bead that can be used for sorting.

More preferably, an amount of the CD25 Positive Selection Cocktail added is the resuspension volume$\times$50 μL, an amount of the Releasable RAPIDSPHERE™ added is the resuspension volume$\times$30 μL, an amount of the $CD4^+$ T cell enrichment antibody mixture added is the resuspension volume$\times$50 μL, an amount of the magnetic bead-removing buffer added is the resuspension volume$\times$100 μL, and an amount of the $CD127^{high}$-removing antibody mixture added is the resuspension volume$\times$50 μL.

In the method for in vitro expansion of cryopreserved cord blood-derived Tregs with a high recovery rate, preferably, in the expansion culture, cells are added to a 48-well plate at a concentration of $2\times10^5$ to $8\times10^5$/mL per well, and 0.5 mL of the expansion culture medium is added to each well for culture.

Preferably, both the primary culture and the subculture are conducted at 36° C. to 38° C. and 4% to 6% $CO_2$.

Preferably, on day 1 to day 2 after inoculation, 0.5 mL to 1 mL of the expansion culture medium and 100 U/mL to 400 U/mL of recombinant human interleukin-2 (rhIL-2) are added to cells in each well, and then a culture is conducted.

More preferably, 0.5 mL of a medium in each well is removed, the remaining medium is thoroughly mixed with cells, cells in each well are passaged to 2 wells, and the medium is supplemented to 1 mL per well; and when the subculture is conducted a third time, the anti-CD3CD28 magnetic beads are removed, and then fresh anti-CD3CD28 magnetic beads are added with a number ratio of the magnetic beads to Tregs being 1:1.

In the method for in vitro expansion of cryopreserved cord blood-derived Tregs with a high recovery rate, preferably, in the expansion culture medium, IL-2 is further added; and more preferably, a concentration of the IL-2 in the expansion culture medium is 10 U/mL to 1,000 U/mL and preferably 200 U/mL to 600 U/mL.

Compared with the prior art, the present disclosure has the following beneficial effects:

1. The method of the present disclosure can achieve the second recovery and expansion of cryopreserved Tregs produced after the first expansion. Tregs produced after the second recovery and expansion can have a viability of 90% or more, and can be further expanded (such as third expansion and fourth expansion). The expanded cells can also be used for clinical treatment. Therefore, the method of the present disclosure greatly shortens the time for clinical patients to wait for Tregs, and can meet the clinical on-demand access requirement.

2. Flow cytometry results of cord blood-derived Tregs produced after the second expansion in the present disclosure show that, after the second expansion, a proportion of $CD4^+CD25^+CD127^-$ cells is 99.6+0.15%, and a proportion of $CD3^+CD8^+$ cells is less than 5%, indicating that a quality of the Tregs meets the standards of clinical research. Carboxyfluorescein diacetate succinimidyl ester (CFSE) assay results show that cord blood-derived Tregs produced after the second expansion still can significantly inhibit the proliferation ability of aggressive T cells.

BRIEF DESCRIPTION OF THE DRAWINGS

To describe the technical solutions in the embodiments of the present disclosure or in the prior art clearly, the accompanying drawings required for describing the embodiments or the prior art will be briefly described below. Apparently, the accompanying drawings in the following description show some embodiments of the present disclosure, and a person of ordinary skill in the art may still derive other accompanying drawings from these accompanying drawings without creative efforts.

FIGS. 6A-6E show inhibitory effects of expanded cord blood-derived Tregs on aggressive T cells (CD4+CD25−) of diabetes in a preferred embodiment of the present disclosure, where FIG. 6A shows an inhibitory effect of a negative control group; FIG. 6B shows an inhibitory effect of a positive control group; FIG. 6C shows an inhibitory effect of a combination of CD25−T cells and Tregs in 1:1; FIG. 6D shows an inhibitory effect of a combination of CD25−T cells and Tregs in 2:1; and FIG. 6E shows an inhibitory effect of a combination of CD25−T cells and Tregs in 4:1.

DETAILED DESCRIPTION OF THE EMBODIMENTS

Figure 1:
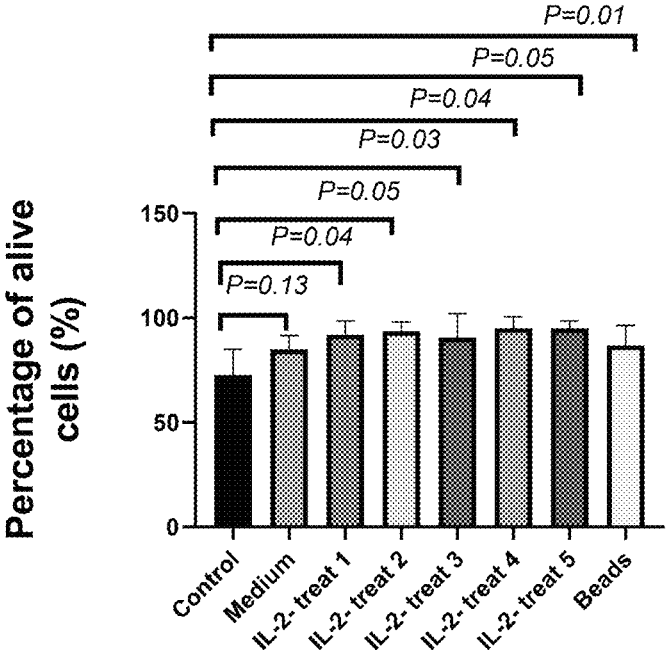
FIG. 1 and FIG. 2 show the comparison of cell recovery viabilities of cryopreserved Tregs in different media (an X-VIVO medium, an expansion culture medium, and IL-2-containing expansion culture media (IL-2 treatment groups with different concentrations are set) and an expansion culture medium+magnetic beads.
Figure 2:
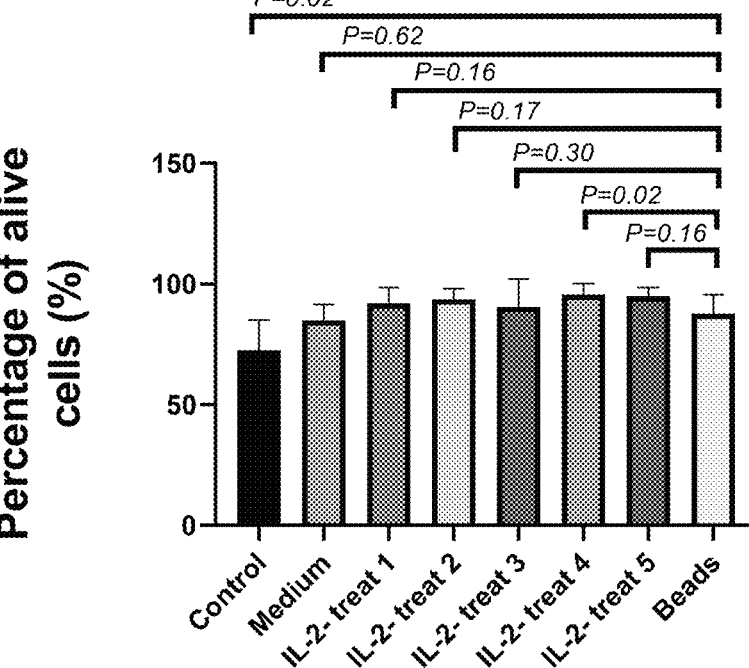
Figure 3:
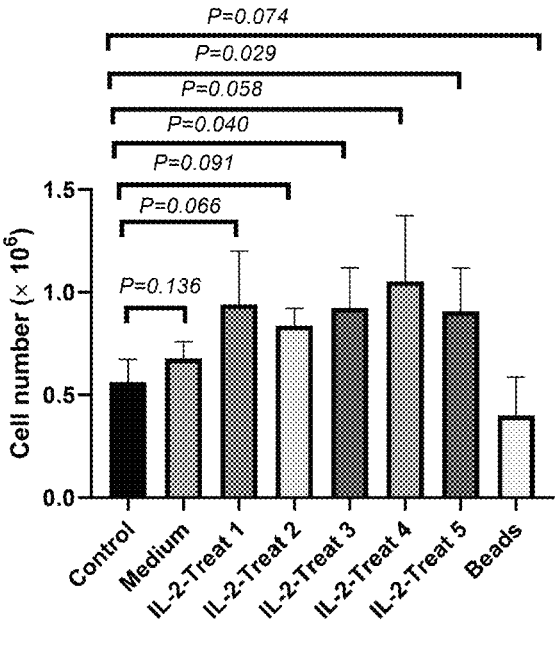
FIG. 3 and FIG. 4 show the comparison of cell numbers of cryopreserved Tregs in different media (an X-VIVO medium, an expansion culture medium, and IL-2-containing expansion culture media (IL-2 treatment groups with different concentrations are set) and an expansion culture medium+magnetic beads.
Figure 4:
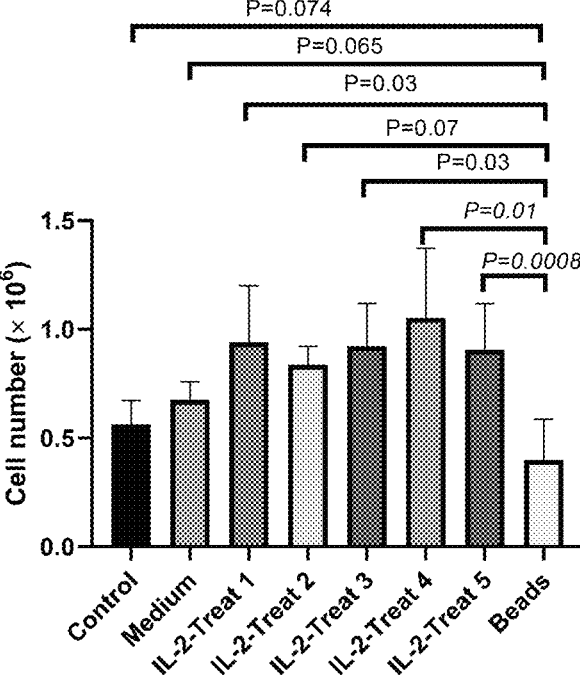

In order to facilitate the understanding of the present disclosure, the present disclosure is described in detail below in conjunction with the accompanying drawings of the specification and the preferred embodiments, but the protection scope of the present disclosure is not limited to the following specific embodiments.

Unless otherwise defined, all technical terms used hereinafter have the same meaning as commonly understood by those skilled in the art. The technical terms used herein are merely for the purpose of describing specific embodiments, and are not intended to limit the protection scope of the present disclosure.

Unless otherwise specified, various raw materials, reagents, instruments, devices, etc. used in the present disclosure can be purchased from the market or can be prepared by the existing methods.

Embodiments

A method for in vitro expansion of cryopreserved cord blood-derived Tregs with a high recovery rate was provided. With the method, Tregs could be subjected to recovery and expanded culture and then used in the preparation of a drug for treating an immune disease. The in vitro expansion method was as follows:

I. Preparation of Cord Blood-Derived Tregs

1. Sterilization of a cord blood bag and preparation of cord blood-derived autologous plasma: Cord blood in the cord blood bag was transferred into a 50 mL centrifuge tube and centrifuged under the following conditions: 20° C., 3,000 rpm, 10 min, +8, and −9. A resulting supernatant was collected and transferred to a new 50 mL centrifuge tube and further centrifuged under the following conditions: 20° C., 4,000 rpm, 10 min, +8, and −9. Resulting yellow clear plasma was collected, inactivated in a 56° C. water bath for 30 min, and then placed in a refrigerator for later use. The remaining cord blood was resuspended with normal saline in the same volume as the collected plasma.

2. The cord blood resuspended in normal saline was slowly added to a lymphocyte separation solution (a volume of the cord blood: a volume of the lymphocyte separation solution=1:1), and centrifugation was conducted under the following conditions: 20° C., *400 rcf to *1610 rcf, 25 min, +0, and −0. After the centrifugation was completed, the cord blood was layered. A PBMC layer was slowly and gently collected with a pipette, where a lymphocyte liquid should be pipetted as little as possible. 3. The PBMC layer was further centrifuged under the following conditions: 20° C., *580 rcf, 10 min, +8, and −9.5 mL to 10 mL of a 10× red blood cell lysis buffer and 45 mL of sterilized water were taken and prepared into a red blood cell lysis buffer. After the centrifugation was completed, a resulting supernatant was removed, and the red blood cell lysis buffer was added. 2 min to 10 min later, 0.9% normal saline was added to 35 mL to stop the red blood cell lysis. Centrifugation was conducted under the following conditions: 20° C., *290 rcf, 10 min, +8, and −9. A resulting supernatant was removed. The steps of adding 0.9% normal saline to a specified volume, centrifugation, and removing a resulting supernatant were repeated 2 times to 3 times.

4. After a supernatant produced after the final centrifugation was removed, resulting cells were loosened by flicking, 0.9% normal saline was added, and 10 μL of a resulting cell solution was taken for counting. 0.9% normal saline was added to the remaining cells to 40 mL. Centrifugation was further conducted under the following conditions: 20° C., *290 rcf, 10 min, +8, and −9. The counting was conducted through the following specific steps: The cell solution taken was added to an EPPENDORF™ (EP) tube, 90 μL of trypan blue was added to the EP tube, and thorough mixing was conducted. 10 μL of a resulting mixture was taken and added to a hemacytometer, and quickly counted: (sum of numbers in four corners/4)×$10^5$ cells/mL*dilution factor. For cells on lines, cells on the upper and left lines were counted, and cells on the lower and right lines were not counted.

5. After the centrifugation was completed, a resulting supernatant was removed, the residual supernatant could be removed by a pipette (1,000 μL) as much as possible, and cells were loosened by flicking. 3 mL of a cryopreservation solution was slowly added dropwise to the cells and gently pipetted up and down for thorough mixing. The remaining cryopreservation solution was added and pipetted up and down for thorough mixing. A resulting cell suspension was added to 5 mL freezing tubes at 4 mL/tube, programmed cooled to −80° C., and transferred to a liquid nitrogen tank. A preparation process of the cryopreservation solution was as follows: according to the cell number of $5×10^6$ to $10×10^6$/mL, a total of 40 mL of the cryopreservation solution was prepared with 90% of cord blood-derived autologous plasma and 10% of dimethyl sulfoxide (DMSO). During the preparation, the autologous plasma was added first and then DMSO was slowly added dropwise. DMSO was taken from bottom to top to prevent coagulation. The whole preparation process was conducted in the dark on ice.

6. A freezing tube with cryopreserved cells was taken out from the liquid nitrogen tank and immediately placed in a 37° C. water bath for recovery. The cells were resuspended with a serum-free medium in a 15 mL centrifuge tube, counted according to the method in the step 4, and then centrifuged under the following conditions: 20° C., *150 rcf to *390 rcf, 10 min, +8, and −9.

7. After the centrifugation was completed, a resulting supernatant was removed. 90 μL of MACS Buffer was added per $1×10^7$ cells/mL, that is, (n×90) μL. 10 μL to 20 μL of CD25 MicroBeadsII was added per $1×10^7$ cells/mL, that is, (n×10) μL. Vortexing was conducted.

8. Cells were resuspended with an Easy Buffer to produce 0.5 mL to 6 mL of a cell suspension with a cell concentration of $5×10^7$ cells/mL.

9. The cell suspension produced after the resuspending was transferred into a sterile tube matching with a magnetic pole.

10. A CD25-positive selection antibody was added at an amount of the resuspension volume×50 μL, and thorough mixing was conducted.

11. Incubation was conducted for 5 min.

12. Releasable spheres were vortexed for 30 s or more until magnetic bead aggregates disappeared.

13. The releasable spheres were added at an amount of the resuspension volume×30 μL, and thorough mixing was conducted.

14. A CD4+T cell enrichment antibody mixture (T cell Enrichment Cocktail) was added at an amount of the resuspension volume×50 μL, and thorough mixing was conducted.

15. Incubation was conducted for 5 min.

16. An Easy Buffer was added to 10 mL, and gentle mixing was conducted 2 times to 3 times.

17. The sterile tube was placed on the magnetic pole without a cap.

18. Incubation was conducted for 10 min.

19. A centrifuge tube was prepared to collect CD25− cells, and a liquid in the sterile tube was poured into the centrifuge tube under the magnetic pole.

20. The sterile tube was removed from the magnetic pole, 10 mL of an Easy Buffer was added, and gentle mixing was conducted 2 times to 3 times. The sterile tube was placed on the magnetic pole, and incubation was conducted for 5 min.

21. The steps 19 and 20 were repeated twice.

22. An Easy Buffer was added to the initial resuspension volume with all cells on a tube wall rinsed off.

23. A magnetic bead-removing buffer (Release Buffer) was added at an amount of the resuspension volume×100 μL, and vigorous mixing was conducted 5 or more times.

24. A CD127$^{high}$-removing antibody mixture (Depletion Cocktail) was added at an amount of the resuspension volume×50 μL, and thorough mixing was conducted.

25. Incubation was conducted for 5 min.

26. An Easy Buffer was added to 10 mL, and thorough mixing was conducted 2 times to 3 times.

27. The sterile tube was placed on the magnetic pole, and incubation was conducted for 5 min.

28. A centrifuge tube was prepared to collect Tregs, and a liquid in the sterile tube was poured into the prepared centrifuge tube under the magnetic pole to obtain the Tregs.

The above process for acquiring Tregs could adopt a EasySep™ human CD4$^+$CD25$^+$CD127$^-$ Treg sorting kit, with brand: STEMCELL™ Technologies and Item No.: 18063. Further the Easy Buffer™ used herein is EasySep™ Buffer, manufactured by STEM CELL Technologies.

II. Expansion of Tregs

1. Cells were inoculated into a 48-well plate at 2×10$^5$ to 8×10$^5$/mL, 0.5 mL of an expansion culture medium including magnetic beads (a number of the magnetic beads: a number of cells=1:1) was added per well on day 0 (a formula of the expansion culture medium was shown in Table 1), and the cells were cultured at 37° C. and 5% $CO_2$.

culture medium was thoroughly mixed with cells, and cells in each well were passaged to 2 wells. An expansion culture medium including 100 U/mL to 400 U/mL of rhIL-2 was added to 1 mL, and cells were cultured at 37° C. and 5% $CO_2$.

5. On day 7 to day 10 after the inoculation, a third passage was conducted as follows: The anti-CD3CD28 magnetic beads in a Petri dish were removed, and then washed fresh anti-CD3CD28 magnetic beads (a number of the magnetic beads: a number of Tregs=1:1) were added. Cells were cultured at 37° C. and 5% $CO_2$.

6. On day 10 to day 11 after the inoculation, a fourth passage was conducted as follows: 0.5 mL of the expansion culture medium was removed, the remaining expansion culture medium was thoroughly mixed with cells, and cells in each well were passaged to 2 wells. An expansion culture medium including 100 U/mL to 400 U/mL of rhIL-2 was added to 1 mL, and cells were cultured at 37° C. and 5% $CO_2$.

7. On day 11 to day 12 after the inoculation, a fifth passage was conducted as follows: 0.5 mL of the expansion culture medium was removed, the remaining expansion culture medium was thoroughly mixed with cells, and cells in each well were passaged to 2 wells. An expansion culture medium including 100 U/mL to 400 U/mL of rhIL-2 was added to 1 mL, and cells were cultured at 37° C. and 5% $CO_2$.

8. On day 12 to day 13 after the inoculation, a sixth passage was conducted as follows: 0.5 mL of the expansion culture medium was removed, the remaining expansion culture medium was thoroughly mixed with cells, and cells

TABLE 1

Formula of 50 mL of the expansion culture medium for cord blood-derived Tregs

| Reagent name | Company | Item No. | Volume | Final concentration |
|---|---|---|---|---|
| X-VIVO 15 w/o Gent or Phenol Red | Lonza | 04-744Q | 35.274 ml-42.69 ml | 70.54%-85.27% |
| Hepes | Hyclone | SH3023701 | 1.25 ml-2.5 ml | 2.5%-5% |
| PENICILLIN STREPTOMYCIN | Gibco | 15140122 | 0.5 ml-1 ml | 1%-2% |
| L-Glutamine solution | sigma | G7513-100ML | 0.5 ml-1 ml | 1%-2% |
| 1000X 2-Mercaptoethanol | Millipore | ES-007-E | 50 μl-100 μl | 50-100 umol/L |
| rhIL-2 | R&D | 202-IL-010 | 7.69 μl-15.4 μl | 200-400 U/ml |
| rapamycin | sigma | R8781-200UL | 1 μl-10 μl | 50-200 nmol/L |
| AB serum | Gemini | 100-512 | 5 ml-10 ml | 10%-20% |

2. On day 1 to day 2 after the inoculation (24 h to 48 h later), 0.5 mL to 1 mL of the expansion culture medium and 100 U/mL to 400 U/mL of rhIL-2 were added to cells in each well, and cells were cultured at 37° C. and 5% $CO_2$.

3. On day 3 to day 4 after the inoculation, a first passage was conducted as follows: 0.5 mL of the expansion culture medium was removed, the remaining expansion culture medium was thoroughly mixed with cells, and cells in each well were passaged to 2 wells. An expansion culture medium including 100 U/mL to 400 U/mL of rhIL-2 was added to 1 mL, and cells were cultured at 37° C. and 5% $CO_2$. After the addition, there was 1 mL of the expansion culture medium in each well, and the content of rhIL-2 added was based on 1 mL of the expansion culture medium. The amounts of rhIL-2 added in other steps were the same as the amount in this step.

4. On day 5 to day 6 after the inoculation, a second passage was conducted as follows: 0.5 mL of the expansion culture medium was removed, the remaining expansion in each well were passaged to 2 wells. An expansion culture medium including 100 U/mL to 400 U/mL of rhIL-2 was added to 1 mL, and cells were cultured at 37° C. and 5% $CO_2$.

9. On day 13 to day 14 after the inoculation, a seventh passage was conducted as follows: 0.5 mL of the expansion culture medium was removed, the remaining expansion culture medium was thoroughly mixed with cells, and cells in each well were passaged to 2 wells. An expansion culture medium including 100 U/mL to 400 U/mL of rhIL-2 was added to 1 mL, and cells were cultured at 37° C. and 5% $CO_2$.

10. On day 14 to day 16 after the inoculation, an eighth passage was conducted as follows: 0.5 mL of the expansion culture medium was removed, the remaining expansion culture medium was thoroughly mixed with cells, and cells in each well were passaged to 2 wells. An expansion culture medium including 100 U/mL to 400 U/mL of rhIL-2 was added to 1 mL, and cells were cultured at 37° C. and 5% $CO_2$.

11. On day 16 to day 18 after the inoculation, a ninth passage was conducted as follows: 0.5 mL of the expansion culture medium was removed, the remaining expansion culture medium was thoroughly mixed with cells, and cells in each well were passaged to 2 wells. An expansion culture medium including 100 U/mL to 400 U/mL of rhIL-2 was added to 1 mL, and cells were cultured at 37° C. and 5% $CO_2$.

In this embodiment, contents of components in the expansion culture medium for Tregs were expressed in volume fractions. A volume fraction refers to a volume proportion of each component. The expansion culture medium for Tregs included 70.54% to 85.27% of a serum-free medium, 2.5% to 5% of a 4-hydroxyethylpiperazine ethanesulfonic acid buffer, 1% to 2% of a penicillin-streptomycin solution, 1% to 2% of L-glutamine, 50 μmol/L to 100 μmol/L of 2-mercaptoethanol, 0 U/mL to 1,000 U/mL of recombinant IL-2, 50 nmol/L to 200 nmol/L of rapamycin, and 10% to 20% of AB serum.

The serum-free medium could be X-VIVO 15 w/o Gent or Phenol Red of Lonza, Item No.: 04-744Q. The 4-hydroxy-ethylpiperazine ethanesulfonic acid buffer could be a Hepes buffer of Hyclone, Item No.: SH3023701. The penicillin-streptomycin solution could be PENICILLIN STREPTO-MYCIN of Gibco, 15140122. The L-glutamine could be an L-glutamine solution of sigma, Item No.: G7513-100ML. The 2-mercaptoethanol could be 1000X 2-Mercaptoethanol of Millipore, Item No.: ES-007-E. The recombinant IL-2 could be rhrhIL-2 of R&D, Item No.: 202-IL-010. The rapamycin could be rapamycin of sigma, Item No.: R8781-200UL. Of course, the same products produced by other companies could also be adopted. The AB serum was from Gemini, USA, Item No.: 100-512.

A preparation method of the above expansion culture medium slightly varied according to the specific use. For example, when Tregs were recovered and inoculated into a plate, the components of the expansion culture medium could be thoroughly mixed in advance and then directly added to a well plate, or the components other than the recombinant IL-2 for the expansion culture medium could be mixed to produce a premix and then the recombinant IL-2 was added. Because the recombinant IL-2 was basically exhausted in each well during the subculture, in the passage from 1 well to 2 wells, the premix was supplemented to each well. For example, 0.5 mL of the premix was supplemented to 1 mL of a solution in each well. In this case, the corresponding recombinant IL-2 should be added based on the amount of the expansion culture medium: 1 mL.

Criteria for the above expansion culture test were as follows:

Cord blood-derived Tregs to be recovered were divided into the following groups with a same cell number: an X-VIVO medium group (control), an expansion culture medium group, IL-2-containing expansion culture medium groups (IL-2 treatment groups with different concentrations: Treat 1:10 U/mL to 75 U/mL; Treat 2:50 U/mL to 150 U/mL; Treat 3:100 U/mL to 250 U/mL; Treat 4:200 U/mL to 600 U/mL; and Treat 5:300 U/mL to 1,000 U/mL), and an expansion culture medium+magnetic bead group. Cells were inoculated into a 48-well plate at $1\times10^6$ cells/well/mL for recovery. The cells were cultured for 48 h in an environment at 36° C. to 38° C. and 4% to 6% $CO_2$, and a cell viability and a cell number were measured. Then the cell expansion was conducted according to the established expansion conditions. A formula of the expansion culture medium was as follows: 42.69 parts of a serum-free medium, 1.25 parts of a 4-hydroxyethylpiperazine ethanesulfonic acid buffer, 0.5 part of a penicillin-streptomycin solution, 0.5 part of L-glutamine, 0.05 part of 2-mercaptoethanol, 0.01154 part of recombinant IL-2, 0.001 part of rapamycin, and 5 parts of AB serum.

There was a same initial number of Tregs for the groups, which was $1\times10^6$. A number of Tregs in each group was counted. The counting was conducted through the following specific steps: 10 μL of a cell suspension was taken and added to an EP tube, 90 μL of trypan blue was added to the EP tube, and thorough mixing was conducted. 10 μL of a resulting mixture was taken and added to a hemacytometer, and quickly counted: (sum of numbers in four corners/4)× $10^5$ cells/mL*dilution factor. For cells on lines, cells on the upper and left lines were counted, and cells on the lower and right lines were not counted. Living and dead cells were determined by trypan blue staining and flow cytometry, and blue-stained and positive cells were dead cells.

After the 48 h cell recovery, in the X-VIVO medium group, the expansion culture medium group, the IL-2-containing expansion culture medium groups (IL-2 treatment groups with different concentrations: 10 U to 1,000 U), and the expansion culture medium+magnetic bead group, viable cell proportions were as follows: Control: 72.54±12.6%; Medium: 84.89±6.73%; IL-2 treat 1:91.96±6.57%; IL-2 treat 2:93.71±4.36%; IL-2 treat 3:90.62±11.44%; IL-2 treat 4:95.03±5.56%; IL-2 treat 5:94.93±3.6%; and Beads: 86.85±9.5%, respectively, and cell numbers (×$10^6$) were as follows: Control: 0.56±0.11; Medium: 0.68±0.081; IL-2 treat 1:0.94±0.26; IL-2 treat 2:0.84±0.083; IL-2 treat 3:0.92±0.197; IL-2 treat 4:1.05±0.32; IL-2 treat 5:0.91±0.21; and Beads: 0.4±0.187, respectively. The results indicated that the traditional direct magnetic bead stimulation method was not suitable for the expansion of cryopreserved Tregs, and the 48 h in vitro recovery with the IL-2-containing expansion culture medium could protect the viability of cells. It can be seen that the expansion culture medium of the present application could significantly promote the proliferation ability of cord blood-derived Tregs, and an appropriate concentration of IL-2 was 200 U/mL to 600 U/mL.

A total number of Tregs in the IL-2-containing expansion culture medium group was $3\times10^7$ on day 21 of expansion. Results of flow cytometry-based phenotypic and functional assays showed that the expanded Tregs had an immunosuppressive ability and met the standard of clinical research.

Experiment 1: a Phenotype of Cord Blood-Derived Tregs was Stable after Expansion 1. One well of Tregs ($5\times10^5$ to $10\times10^5$) were taken, and 0.9% normal saline was added to 5 mL (room temperature). Centrifugation was conducted under the following conditions: 20° C., *570 rcf, 5 min, +8, and −9.

2. A phenotype of Tregs was detected with a PerFix-nc Kit (Item No.: PN B10825, Beckman). This kit included the following three buffers: buffer 1: Fixative Reagent, PN B10827-75tests-liquid; buffer 2: Permeabilizing Reagent, PN B10828-75tests-liquid; and buffer 3: Final 10×Solution, PN B10829-75tests-liquid. A supernatant produced after the centrifugation was removed by a pipette tip with 50 μL to 100 μL of a liquid left, and then 5 μL of the buffer 1 and 5 μL of an Fc Block antibody were added. Shaking was conducted (moderately), and incubation was conducted at room temperature in the dark for 15 min.

3. 5 μL of each of CD4, CD25, and CD127 antibodies was added. Shaking was conducted (moderately), and incubation was conducted at room temperature in the dark for 15 min to 30 min.

4. 3 mL of the buffer 3 diluted into a working solution (buffer 3: water=1:9) was added. Centrifugation was conducted under the following conditions: 20° C., *570 rcf, 5 min, +8, and −9.

5. Flow cytometry was conducted. Flow cytometry results showed that, on day 18 of expansion, a proportion of CD4$^+$CD25$^+$CD127$^-$ cells was 97.07+2.03% and a proportion of CD3+CD8+ cells was 4.69+2.0%, indicating that a quality of the Tregs reached the standard of clinical research.

Experiment 2: Cord Blood-Derived Tregs could Significantly Inhibit the Proliferation Ability of Aggressive T Cells after Expansion 1. CD4(+)CD25(−) aggressive T cells were recovered, and 1×10$^6$ cells were taken.

2. The cells (1×10$^6$ cells) were resuspended with 1 mL of a serum-free medium.

3. 1 μL of a cell trace stock solution was added per 1 mL of a cell suspension (CellTrace™ CFSE Cell Proliferation Kit, Item No.: C34554, Thermofisher scientific. This kit included 10 parts of single-use bottled CellTrace™ CFSE (component A) and 1 part of bottled DMSO (component B). The cell trace stock solution was a mixed solution of 18 μL of DMSO and one part of bottled CellTrace™ CFSE prepared according the instructions of the kit for CFSE staining of cells. Details could be seen on thermofisher.com.

4. Incubation was conducted for 20 min at 37° C. in the dark.

5. 5 mL of a washing solution (serum-free medium+10% fetal bovine serum (FBS) was added.

6. Incubation was conducted for 5 min at 37° C. in the dark.

7. Centrifugation was conducted under the following conditions: 20° C., *290 rcf, 10 min, +8, and −9.

8. Cells were resuspended with a medium (serum-free medium+10% FBS) pre-warmed at 37° C.

9. One well of Tregs were taken, subjected to magnetic bead removal, counted, and centrifuged under the following conditions: 20° C., *290 rcf, 10 min, +8, and −9.

10. 1×10$^6$ Tregs were resuspended with a medium (serum-free medium+10% FBS) pre-warmed at 37° C.

11. CD4(+)CD25− T cells and Tregs were co-cultured in a 96-well plate with a number ratio of the CD4(+)CD25− T cells to the Tregs being 1:1, 2:1, and 4:1 (in each well, there was 200 μL in total, and 3 μL of magnetic beads was added). A CD4(+)CD25− T cell group treated with CFSE alone was set as a negative control group, and a CD4(+)CD25− T cell group treated with CFSE (magnetic bead stimulation) was set as a positive control group.

12. An inhibitory function of cord blood-derived Tregs was detected by flow cytometry.

13. Results of the CFSE experiment showed that, when CD4(+) CD25−T cells and Tregs were co-cultured in number ratios of 1:1, 2:1, and 4:1, inhibitory rates for the proliferation of CD4(+) CD25− T cells were 77.27±15.5%, 74.53±18.36%, and 74±17.1%, respectively. The results indicated that the expanded cord blood-derived Tregs could significantly inhibit the proliferation ability of aggressive T cells.

III. Cryopreservation and Recovery of Expanded Tregs

1. Tregs produced after 14 d to 21 d of expansion were collected in a centrifuge tube with an expansion culture medium. Centrifugation was conducted, a resulting supernatant was removed, and resulting cells were loosened by flicking. 0.9% normal saline was added, and 10 μL of a resulting cell solution was taken for counting. 0.9% normal saline was added to the remaining cells to 40 mL. Centrifugation was further conducted under the following conditions: 20° C., *290 rcf, 10 min, +8, and −9. The counting was conducted through the following specific steps: The cell solution taken was added to an EP tube, 90 μL of trypan blue was added to the EP tube, and thorough mixing was conducted. 10 μL of a resulting mixture was taken and added to a hemacytometer, and quickly counted: (sum of numbers in four corners/4)×10$^5$ cells/mL*dilution factor. For cells on lines, cells on the upper and left lines were counted, and cells on the lower and right lines were not counted.

2. After the centrifugation was completed, a resulting supernatant was removed, the residual supernatant could be removed by a pipette (1,000 μL) as much as possible, and cells were loosened by flicking. 3 mL of a cryopreservation solution was slowly added dropwise to the cells and gently pipetted up and down for thorough mixing. The remaining cryopreservation solution was added and pipetted up and down for thorough mixing. A resulting cell suspension was added to 5 mL freezing tubes at 4 mL/tube, programmed cooled to −80° C., and transferred to a liquid nitrogen tank. A preparation process of the cryopreservation solution was as follows: according to the cell number of 5×10$^6$ to 10×10$^6$/mL, a total of 40 mL of the cryopreservation solution was prepared with 90% of AB serum and 10% of DMSO. During the preparation, the autologous plasma was added first and then DMSO was slowly added dropwise. DMSO was taken from bottom to top to prevent coagulation. The whole preparation process was conducted in the dark on ice.

3. A freezing tube with cryopreserved cells was taken out from the liquid nitrogen tank and immediately placed in a 37° C. water bath for recovery. The cells were resuspended with a serum-free medium in a 15 mL centrifuge tube, counted according to the method in the step 1, and then centrifuged under the following conditions: 20° C., *150 rcf to *390 rcf, 10 min, +8, and −9.

4. Cells were inoculated into a 48-well plate at 2×10$^5$ to 8×10$^5$/mL, 0.5 mL of an expansion culture medium including 10 U/mL to 2,000 U/mL of rhIL-2 was added per well on day 0, and the cells were cultured at 37° C. and 5% CO$_2$.

5. On day 1 to day 3 after inoculation (24 h to 72 h later), a viability and number of cells were detected with trypan blue (a detailed method could be seen in the step 4 of "I. Preparation of cord blood-derived Tregs"), as shown in FIG. 1 to FIG. 4. 0.5 mL to 1 mL of an expansion culture medium, magnetic beads (a number of the magnetic beads: a number of cells=1:1), and 100 U/mL to 400 U/mL of rhIL-2 were added to cells in each well, and cells were cultured at 37° C. and 5% CO$_2$.

6. On day 3 to day 4 after the inoculation, a first passage was conducted as follows: 0.5 mL of the expansion culture medium was removed, the remaining expansion culture medium was thoroughly mixed with cells, and cells in each well were passaged to 2 wells. An expansion culture medium including 100 U/mL to 400 U/mL of rhIL-2 was added to 1 mL, and cells were cultured at 37° C. and 5% CO$_2$. After the addition, there was 1 mL of the expansion culture medium in each well, and the content of rhIL-2 added was based on 1 mL of the expansion culture medium. The amounts of rhIL-2 added in other steps were the same as the amount in this step.

7. On day 5 to day 6 after the inoculation, a second passage was conducted as follows: 0.5 mL of the expansion culture medium was removed, the remaining expansion culture medium was thoroughly mixed with cells, and cells in each well were passaged to 2 wells. An expansion culture medium including 100 U/mL to 400 U/mL of rhIL-2 was added to 1 mL, and cells were cultured at 37° C. and 5% $CO_2$.

8. On day 7 to day 10 after the inoculation, a third passage was conducted as follows: The anti-CD3CD28 magnetic beads in a Petri dish were removed, and then washed fresh anti-CD3CD28 magnetic beads (a number of the magnetic beads: a number of Tregs=1:1) were added. Cells were cultured at 37° C. and 5% $CO_2$.

9. On day 10 to day 11 after the inoculation, a fourth passage was conducted as follows: 0.5 mL of the expansion culture medium was removed, the remaining expansion culture medium was thoroughly mixed with cells, and cells in each well were passaged to 2 wells. An expansion culture medium including 100 U/mL to 1,000 U/mL of rhIL-2 was added to 1 mL, and cells were cultured at 37° C. and 5% $CO_2$.

10. On day 11 to day 12 after the inoculation, a fifth passage was conducted as follows: 0.5 mL of the expansion culture medium was removed, the remaining expansion culture medium was thoroughly mixed with cells, and cells in each well were passaged to 2 wells. An expansion culture medium including 100 U/mL to 1,000 U/mL of rhIL-2 was added to 1 mL, and cells were cultured at 37° C. and 5% $CO_2$.

11. On day 12 to day 13 after the inoculation, a sixth passage was conducted as follows: 0.5 mL of the expansion culture medium was removed, the remaining expansion culture medium was thoroughly mixed with cells, and cells in each well were passaged to 2 wells. An expansion culture medium including 100 U/mL to 1,000 U/mL of rhIL-2 was added to 1 mL, and cells were cultured at 37° C. and 5% $CO_2$.

12. On day 13 to day 14 after the inoculation, a seventh passage was conducted as follows: 0.5 mL of the expansion culture medium was removed, the remaining expansion culture medium was thoroughly mixed with cells, and cells in each well were passaged to 2 wells. An expansion culture medium including 100 U/mL to 1,000 U/mL of rhIL-2 was added to 1 mL, and cells were cultured at 37° C. and 5% $CO_2$.

Experiment 3: a Phenotype of Cord Blood-Derived Tregs was Stable after the Second Expansion 1. One well of Tregs ($5 \times 10^5$ to $10 \times 10^5$) were taken, and 0.9% normal saline was added to 5 mL (room temperature). Centrifugation was conducted under the following conditions: 20° C., *570 rcf, 5 min, +8, and −9.

2. A phenotype of Tregs was detected with a PerFix-nc Kit (Item No.: PN B10825, Beckman). This kit included the following three buffers: buffer 1: Fixative Reagent, PN B10827-75tests-liquid; buffer 2: Permeabilizing Reagent, PN B10828-75tests-liquid; and buffer 3: Final 10×Solution, PN B10829-75tests-liquid. A supernatant produced after the centrifugation was removed by a pipette tip with 50 μL to 100 μL of a liquid left, and then 5 μL of the buffer 1 and 5 μL of an Fc Block antibody were added. Shaking was conducted (moderately), and incubation was conducted at room temperature in the dark for 15 min.

3. 5 μL of each of CD4, CD25, and CD127 antibodies was added. Shaking was conducted (moderately), and incubation was conducted at room temperature in the dark for 15 min to 30 min.

4. 3 mL of the buffer 3 diluted into a working solution (buffer 3: water=1:9) was added. Centrifugation was conducted under the following conditions: 20° C., *570 rcf, 5 min, +8, and −9.

Figure 5:
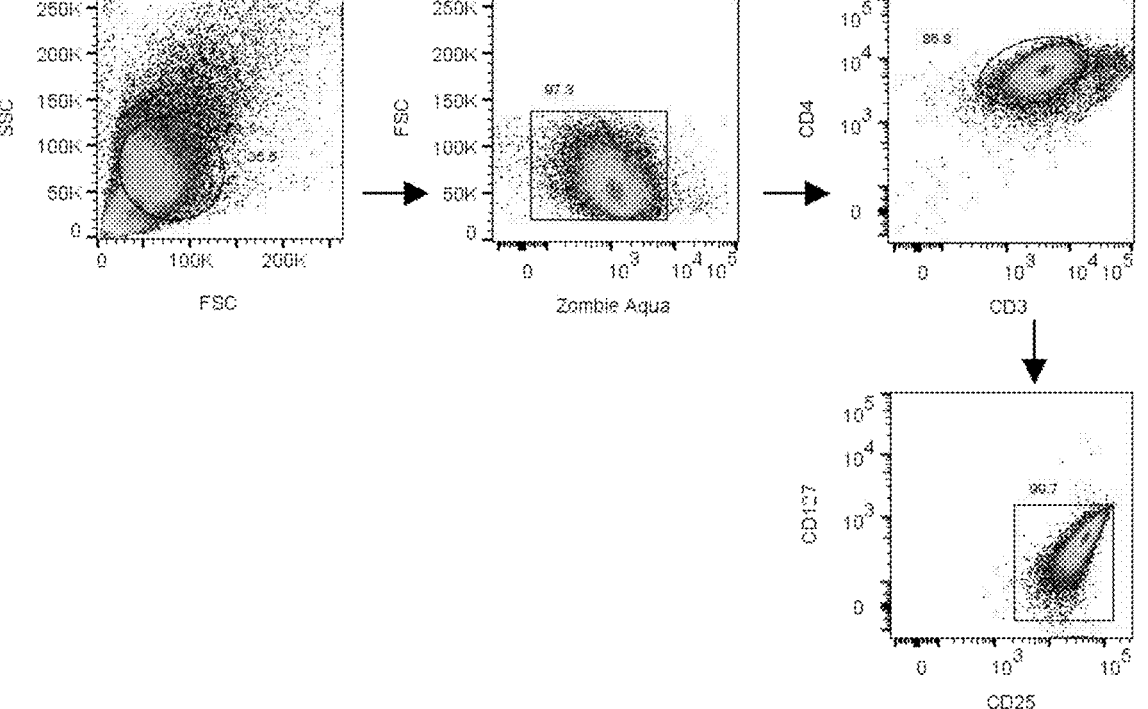
FIG. 5 shows phenotypic detection results of cord blood-derived Tregs produced after second expansion in a preferred embodiment of the present disclosure.
Figures 6D, 6E:
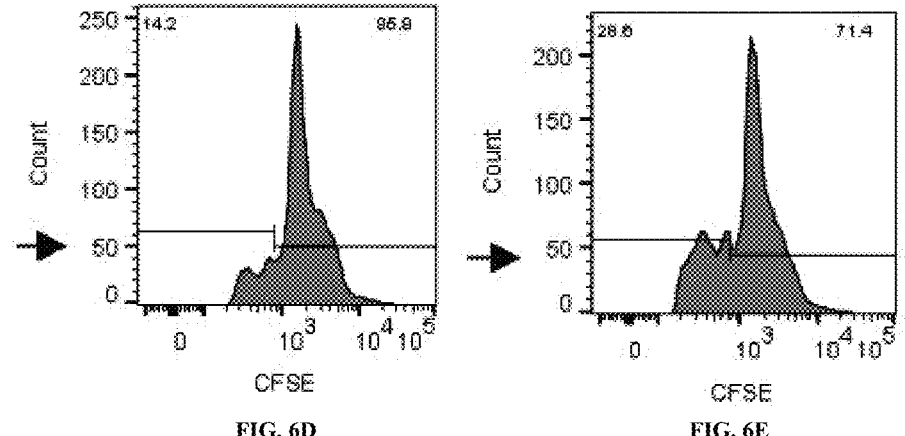

5. Flow cytometry was conducted. Flow cytometry results showed that, after the expansion, a proportion of $CD4^+$ $CD25^+CD127^-$ cells was 99.6+0.15% and a proportion of $CD3^+CD8^+$ cells was less than 5%, indicating that a quality of the Tregs reached the standard of clinical research. Test results were shown in FIG. 5.

Experiment 4: Cord Blood-Derived Tregs could Significantly Inhibit the Proliferation Ability of Aggressive T Cells after the Second Expansion 1. CD4(+)CD25(−) aggressive T cells were recovered, and $1 \times 10^6$ cells were taken.

2. The cells ($1 \times 10^6$ cells) were resuspended with 1 mL of a serum-free medium.

3. 1 μL of a cell trace stock solution was added per 1 mL of a cell suspension (CellTrace™ CFSE Cell Proliferation Kit, Item No.: C34554, Thermofisher™ scientific. This kit included 10 parts of single-use bottled CellTrace™ CFSE (component A) and 1 part of bottled DMSO (component B). The cell trace stock solution was a mixed solution of 18 μL of DMSO and one part of bottled CellTrace™ CFSE prepared according the instructions of the kit for CFSE staining of cells. Details could be seen on thermofisher.com.

4. Incubation was conducted for 20 min at 37° C. in the dark.

5. 5 mL of a washing solution (serum-free medium+10% fetal bovine serum (FBS) was added.

6. Incubation was conducted for 5 min at 37° C. in the dark.

7. Centrifugation was conducted under the following conditions: 20° C., *290 rcf, 10 min, +8, and −9.

8. Cells were resuspended with a medium (serum-free medium+10% FBS) pre-warmed at 37° C.

9. One well of Tregs were taken, subjected to magnetic bead removal, counted, and centrifuged under the following conditions: 20° C., *290 rcf, 10 min, +8, and −9.

10. $1 \times 10^6$ Tregs were resuspended with a medium (serum-free medium+10% FBS) pre-warmed at 37° C.

11. CD4(+)CD25− T cells and Tregs were co-cultured in a 96-well plate with a number ratio of the CD4(+)CD25− T cells to the Tregs being 1:1, 2:1, and 4:1 (in each well, there was 200 μL in total, and 3 μL of magnetic beads was added). A CD4(+)CD25− T cell group treated with CFSE alone was set as a negative control group, and a CD4 (+) CD25-T cell group treated with CFSE (magnetic bead stimulation) was set as a positive control group.

12. An inhibitory function of cord blood-derived Tregs was detected by flow cytometry.

13. Results of the CFSE experiment showed that, when CD4(+)CD25−T cells and Tregs were co-cultured in number ratios of 1:1, 2:1, and 4:1, inhibitory rates for the proliferation of $CD4^{(+)}$ $CD25^-$ T cells were 91.36±4.1%, 83.2±7.4%, and 63±17.4%, respectively. The results indicated that the cord blood-derived Tregs produced after the second expansion could significantly inhibit the proliferation ability of aggressive T cells, as shown in FIGS. 6A-6E.

What is claimed is:

1. A method for in vitro expansion of cord blood-derived regulatory T cells (Tregs), comprising the following steps:

(1) preparing Tregs, adding an expansion culture medium to Tregs carrying magnetic beads, and conducting a first expansion culture, wherein a primary culture is conducted for 1 day to 2 days, then a subculture is conducted once every 1 day to 3 days, and a total culture time is 18 days or more; recovering the cord blood-derived Tregs after the first expansion culture, and resuspending cord blood-derived Tregs with a serum-free medium to produce a suspension; and cryopreserving the Tregs produced after the first expansion culture; wherein a process for the preparing Tregs comprises the following steps:

isolating peripheral blood mononuclear cells (PBMC) from cord blood, removing red blood cells with a red blood cell lysis buffer, washing, and counting the isolated PBMC; conducting centrifugation on the washed and counted PBMC, removing a first resulting supernatant from the centrifuged PBMC, and cryopreserving the centrifuged PBMC after removing the first resulting supernatant; and recovering the cryopreserved PBMC by thawing and counting the recovered PBMC;

conducting centrifugation on the recovered PBMC, removing a second resulting supernatant from the centrifuged PBMC, and resuspending the PBMCs with a magnetic bead to produce 0.5 mL to 6 mL of a cord blood-derived Treg-containing suspension with a cell concentration of $5 \times 10^7$ cells/mL; and transferring the cord blood-derived Treg-containing suspension into a sterile tube contacting a magnetic pole, adding a CD25 selection cocktail to the Treg-containing suspension, and incubating for 5 min; vortexing releasable magnetic bead solution for 30 seconds or more; adding a $CD4^+$ T cell enrichment antibody mixture to the releasable magnetic bead solution, and incubating for 5 min; adding the magnetic bead solution, and mixing 2 times to 3 times; placing the sterile tube on the magnetic pole, and incubating for 10 min; preparing a first centrifuge tube to collect $CD25^-$ cells, and pouring a first liquid in the sterile tube into the first centrifuge tube; removing the sterile tube from the magnetic pole, adding 10 mL of the magnetic bead solution to the sterile tube, mixing 2 times to 3 times, placing the sterile tube on the magnetic pole, and incubating for 5 min; adding the magnetic bead solution to an initial resuspension volume with all cells including cells attached on a tube wall; adding a magnetic bead-removing buffer to the initial resuspension volume that contains the magnetic beads; adding a $CD127^{high}$-removing antibody mixture to the initial resuspension volume that contains the magnetic beads, and incubating for 5 min; adding the magnetic bead solution to the initial resuspension volume that contains the magnetic beads, and mixing 2 times to 3 times; placing the sterile tube on the magnetic pole, and incubating for 5 min; and preparing a second centrifuge tube to collect the Tregs present in the resuspension volume, and pouring a second liquid in the sterile tube into the second centrifuge tube under the magnetic pole to obtain the Tregs; wherein the first expansion culture comprises the following steps:

inoculating the Tregs into a 48-well plate at $2 \times 10^5$ to $8 \times 10^5$/mL, adding 0.5 mL of an expansion culture medium comprising magnetic beads per well on day 0, and culturing at 37° C. and 5% $CO_2$, wherein a number of the magnetic beads: a number of the cells=1:1;

on day 1 to day 2 after the inoculation, adding 0.5 mL to 1 mL of the expansion culture medium and 100

U/mL to 400 U/mL of recombinant human interleukin-2 (rhIL-2) to Tregs in each well, and culturing at 37° C. and 5% $CO_2$;

on day 3 to day 4 after the inoculation, a first passage is conducted as follows: 0.5 mL of the expansion culture medium is removed, a remaining expansion culture medium is thoroughly mixed with cells, and cells in each well are passaged to 2 wells, an expansion culture medium comprising 100 U/mL to 400 U/mL of rhIL-2 is added to 1 mL, and the cells are cultured at 37° C. and 5% $CO_2$; after the addition, 1 mL of the expansion culture medium is presented in each well, and an amount of rhIL-2 added is based on 1 mL of the expansion culture medium, amounts of rhIL-2 added in other steps are equal to the amount in this step;

on day 5 to day 6 after the inoculation, a second passage is conducted as follows: 0.5 mL of the expansion culture medium is removed, a remaining expansion culture medium is thoroughly mixed with cells, and cells in each well are passaged to 2 wells, the expansion culture medium comprising 100 U/mL to 400 U/mL of rhIL-2 is added to 1 mL, and the cells are cultured at 37° C. and 5% $CO_2$;

on day 7 to day 10 after the inoculation, a third passage is conducted as follows: anti-CD3CD28 magnetic beads in a Petri dish are removed, and then washed fresh anti-CD3CD28 magnetic beads are added to Tregs according to a number of the magnetic beads: a number of the Tregs=1:1, and cells are cultured at 37° C. and 5% $CO_2$;

on day 10 to day 11 after the inoculation, a fourth passage is conducted as follows: 0.5 mL of the expansion culture medium is removed, a remaining expansion culture medium is thoroughly mixed with cells, and cells in each well are passaged to 2 wells, the expansion culture medium comprising 100 U/mL to 400 U/mL of rhIL-2 is added to 1 mL, and the cells are cultured at 37° C. and 5% $CO_2$;

on day 11 to day 12 after the inoculation, a fifth passage is conducted as follows: 0.5 mL of the expansion culture medium is removed, a remaining expansion culture medium is thoroughly mixed with cells, and cells in each well are passaged to 2 wells, the expansion culture medium comprising 100 U/mL to 400 U/mL of rhIL-2 is added to 1 mL, and the cells are cultured at 37° C. and 5% $CO_2$;

on day 12 to day 13 after the inoculation, a sixth passage is conducted as follows: 0.5 mL of the expansion culture medium is removed, a remaining expansion culture medium is thoroughly mixed with cells, and cells in each well are passaged to 2 wells, the expansion culture medium comprising 100 U/mL to 400 U/mL of rhIL-2 is added to 1 mL, and the cells are cultured at 37° C. and 5% $CO_2$;

on day 13 to day 14 after the inoculation, a seventh passage is conducted as follows: 0.5 mL of the expansion culture medium is removed, a remaining expansion culture medium is thoroughly mixed with cells, and cells in each well are passaged to 2 wells, the expansion culture medium comprising 100 U/mL to 400 U/mL of rhIL-2 is added to 1 mL, and the cells are cultured at 37° C. and 5% $CO_2$;

on day 14 to day 16 after the inoculation, an eighth passage is conducted as follows: 0.5 mL of the expansion culture medium is removed, a remaining expansion culture medium is thoroughly mixed with cells, and cells in each well are passaged to 2 wells, the expansion culture medium comprising 100 U/mL to 400 U/mL of rhIL-2 is added to 1 mL, and the cells are cultured at 37° C. and 5% $CO_2$; and on day 16 to day 18 after the inoculation, a ninth passage is conducted as follows: 0.5 mL of the expansion culture medium is removed, a remaining expansion culture medium is thoroughly mixed with cells, and cells in each well are passaged to 2 wells, the expansion culture medium comprising 100 U/mL to 400 U/mL of rhIL-2 is added to 1 mL, and the cells are cultured at 37° C. and 5% $CO_2$;

(2) thawing and recovering the ninth passage cryopreserved Tregs from the first expansion culture and adding the recovered Tregs to the expansion culture medium and conducting a second expansion culture; wherein the recovered Tregs exhibit (i) a viability of at least 80% as determined by trypan blue exclusion and (ii) a phenotype of at least 90% CD4+CD25+CD127⁻ by volume cells as determined by flow cytometry, and wherein a primary culture is conducted for 48 hours, then a subculture is conducted once every 1 day to 3 days, and a total culture time is 13 days or more; wherein the second expansion culture comprises the following steps:

inoculating the recovered Tregs into a 48-well plate at $2{\times}10^5$ to $8{\times}10^5$/mL, adding 0.5 mL of an expansion culture medium comprising 200 U/mL to 600 U/mL of rhIL-2 per well on day 0, and culturing at 37° C. and 5% $CO_2$ for 48 hours;

on day 2 to day 3 after the inoculation of the Tregs, detecting a viability and number of Tregs with trypan blue, adding 0.5 mL to 1 mL of the expansion culture medium, the magnetic beads, and 100 U/mL to 400 U/mL of rhIL-2 to Tregs in each well, and culturing at 37° C. and 5% $CO_2$, wherein a number of the magnetic beads: a number of the Tregs=1:1;

on day 3 to day 4 after the inoculation, a first passage is conducted as follows: 0.5 mL of the expansion culture medium is removed, a remaining expansion culture medium is thoroughly mixed with Tregs, and Tregs in each well are passaged to 2 wells, the expansion culture medium comprising 100 U/mL to 400 U/mL of rhIL-2 is added to 1 mL, and the Tregs are cultured at 37° C. and 5% $CO_2$; after the addition, 1 mL of the expansion culture medium is presented in each well, and an amount of rhIL-2 added is based on 1 mL of the expansion culture medium, amounts of rhIL-2 added in other steps are equal to the amount in this step;

on day 5 to day 6 after the inoculation, a second passage is conducted as follows: 0.5 mL of the expansion culture medium is removed, a remaining expansion culture medium is thoroughly mixed with Tregs, and Tregs in each well are passaged to 2 wells, the expansion culture medium comprising 100 U/mL to 400 U/mL of rhIL-2 is added to 1 mL, and the Tregs are cultured at 37° C. and 5% $CO_2$;

on day 7 to day 10 after the inoculation, a third passage is conducted as follows: anti-CD3CD28 magnetic beads in a Petri dish are removed, and then washed fresh anti-CD3CD28 magnetic beads are added according to a number of the magnetic beads: a number of the Tregs=1:1, and Tregs are cultured at 37° C. and 5% $CO_2$;

on day 10 to day 11 after the inoculation, a fourth passage is conducted as follows: 0.5 mL of the expansion culture medium is removed, a remaining expansion culture medium is thoroughly mixed with Tregs, and Tregs in each well are passaged to 2 wells, an expansion culture medium comprising 100 U/mL to 1000 U/mL of rhIL-2 is added to 1 mL, and the Tregs are cultured at 37° C. and 5% $CO_2$;

on day 11 to day 12 after the inoculation, a fifth passage is conducted as follows: 0.5 mL of the expansion culture medium is removed, a remaining expansion culture medium is thoroughly mixed with Tregs, and Tregs in each well are passaged to 2 wells, the expansion culture medium comprising 100 U/mL to 1000 U/mL of rhIL-2 is added to 1 mL, and the Tregs are cultured at 37° C. and 5% $CO_2$;

on day 12 to day 13 after the inoculation, a sixth passage is conducted as follows: 0.5 mL of the expansion culture medium is removed, a remaining expansion culture medium is thoroughly mixed with Tregs, and Tregs in each well are passaged to 2 wells, the expansion culture medium comprising 100 U/mL to 1000 U/mL of rhIL-2 is added to 1 mL, and the Tregs are cultured at 37° C. and 5% $CO_2$; and on day 13 to day 14 after the inoculation, a seventh passage is conducted as follows: 0.5 mL of the expansion culture medium is removed, a remaining expansion culture medium is thoroughly mixed with Tregs, and Tregs in each well are passaged to 2 wells, the expansion culture medium comprising 100 U/mL to 1000 U/mL of rhIL-2 is added to 1 mL, and the Tregs are cultured at 37° C. and 5% $CO_2$;

wherein, according to a final concentration, the expansion culture medium comprises 70.54% to 85.27% volume fraction of the serum-free medium, 2.5% to 5% volume fraction of a 4-hydroxyethylpiperazine ethanesulfonic acid buffer, 1% to 2% volume fraction of a penicillin-streptomycin solution, 1% to 2% volume fraction of L-glutamine, 50 μmol/L to 100 μmol/L of 2-mercaptoethanol, 50 nmol/L to 200 nmol/L of rapamycin, and 10% to 20% volume fraction of AB serum, in addition to the rhIL-2;

the magnetic beads used in the first expansion culture and the second expansion culture are both the anti-CD3CD28 magnetic beads; and a cryopreservation solution used for cryopreserving the Tregs produced after the first expansion culture is 90% by volume of cord blood-derived plasma and 10% by volume of dimethyl sulfoxide (DMSO).

2. The method for the in vitro expansion of the cord blood-derived Tregs according to claim 1, wherein 50 μL of the cocktail added is a resuspension volume, 30 μL of the releasable magnetic bead solution added is the resuspension volume, 50 μL of the CD4+ T cell enrichment antibody mixture added is the resuspension volume, 100 μL of the magnetic bead-removing buffer added is the resuspension volume, and 50 μL of the CD127$^{high}$-removing antibody mixture added is the resuspension volume.

* * * * *